US00PP15897P2

(12) United States Plant Patent
Mowrey et al.

(10) Patent No.: US PP15,897 P2
(45) Date of Patent: Jul. 26, 2005

(54) PLUM TREE NAMED 'SUPLUMTHIRTYFIVE'

(50) Latin Name: *Prunus salicina*
Varietal Denomination: Suplumthirtyfive

(75) Inventors: Bruce D. Mowrey, Watsonville, CA (US); David W. Cain, Bakersfield, CA (US); Terry A. Bacon, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 10/867,613

(22) Filed: Jun. 14, 2004

(51) Int. Cl.[7] ..... A01H 5/00
(52) U.S. Cl. ..... Plt./184
(58) Field of Search ..... Plt./184

(56) References Cited

U.S. PATENT DOCUMENTS

PP4,902 P 10/1982 Weinberger ..... Plt./184
PP5,487 P 6/1985 Weinberger ..... Plt./184

*Primary Examiner*—Anne Marie Grunberg
*Assistant Examiner*—June Hwu
(74) *Attorney, Agent, or Firm*—Knobbe, Martens, Olson & Bear, LLP

(57) ABSTRACT

A new and distinct plum tree variety, *Prunus salicina* 'Suplumthirtyfive,' that is a heavy and consistent producer of early-season (June 16–22) black plums that are larger (66 mm) than other commercial plums in 'Santa Rosa' (unpatented) ripening season. The amber-colored flesh is crisp and juicy with sugar levels (17–19° brix) that are higher than other commercial plum varieties harvested at the same time.

1 Drawing Sheet

Latin name of the genus and species claimed: *Prunus salicina*.
Variety denomination: 'Suplumthirtyfive'.

BACKGROUND OF THE INVENTION

The present invention relates to a new and distinct variety of plum tree, herein after referred to by the cultivar name 'Suplumthirtyfive.' The new variety 'Suplumthirtyfive' originated by hybridization, being first hybridized by Bruce Mowrey and selected by David Cain. The new variety was first evaluated by David Cain and Terry Bacon near Wasco, Calif. in Kern County.

SUMMARY OF THE INVENTION

The new variety 'Suplumthirtyfive' is characterized by possessing black skinned, firm, crisp, yellow-fleshed plums with plentiful juice that ripen early in the season. The skin is of medium thickness with a moderate amount of bloom, and a mildly bitter taste. The fruit production is both heavy and consistent. The plums are large (approximately 66 mm), firm, and have higher sugar levels (approximately 17–19° brix) than other plum varieties ripening during the 'Santa Rosa' (unpatented) ripening season in the San Joaquin Valley, Calif.

The seed parent of the new variety 'Suplumthirtyfive' is '90P-063' (unpatented) that was selected from a progeny of 'Suplumfifteen' (U.S. Plant Pat. No. 5487) crossed with pollen of 'Suplumeleven' (U.S. Plant Pat. No. 4,902). The pollen parent is '91P-083' (unpatented) that was itself selected from a progeny of a cross between two unpatented breeding selections, '232-205' crossed with pollen of '275-136.' The parent varieties were first crossed in March 1994, with the date of planting of February 1995, and the date of first flowering being March 1997. The new plum variety was first asexually propagated by Terry Bacon near Wasco, Kern County, Calif. in 2001, by budding onto 'Nemared' (unpatented) rootstock.

The new variety 'Suplumthirtyfive' is distinguished from its seed parent, '90P-063' in that the new variety ripens approximately 25 days earlier and has amber flesh, while the seed parent has red flesh. The new variety can be distinguished from its pollen parent, '91P-083' in that the new variety ripens 20 days earlier and has amber flesh while the pollen parent has red flesh.

The new plum variety 'Suplumthirtyfive' may be distinguished from presently available cultivars in commerce by the following combination of characteristics: 'Suplumthirtyfive' most closely resembles the commercial plum tree variety, 'Black Amber' (unpatented), but may be distinguished from 'Black Amber' in that the new variety ripens approximately seven days earlier and has a larger fruit diameter (approximately 66 mm compared to approximately 61 mm for 'Black Amber'). The new variety ripens about the same time as the 'Santa Rosa' variety, but has larger fruits with black skin, while 'Santa Rosa' has fruits of approximately 58 mm diameter with red skin.

The new variety 'Suplumthirtyfive' has been shown to maintain its distinguishing characteristics through successive asexual propagations by, for example, budding onto 'Nemared' (unpatented) rootstock.

BRIEF DESCRIPTION OF THE FIGURE

The accompanying color photographic illustration (FIG. 1) shows typical specimens of the foliage and fruit of the new plum variety 'Suplumthirtyfive.' The illustration shows the upper and lower surface of the leaves, an exterior and sectional view of a fruit divided across its suture plane to show flesh color, pit cavity and the stone remaining in place.

The photographic illustration was taken shortly after being picked (shipping ripe) and the colors are as nearly true as is reasonably possible in a color representation of this type.

DETAILED BOTANICAL DESCRIPTION OF THE INVENTION

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The new variety 'Suplumthirtyfive' has not been observed under all possible environmental conditions. The phenotype may vary somewhat with variations in environment such as temperature, daylength, and light intensity, without, however, any variance in genotype.

The descriptive matter which follows pertains to eight year old 'Suplumthirtyfive' plants grown in the vicinity of Wasco, Kern County, Calif., during 2002 and is believed to apply to plants of the variety grown under similar conditions of soil and climate elsewhere.

TREE

General: (measurements taken on 8 year old tree unless otherwise noted).

*Tree size*.—Medium. Normal for most plum varieties. Reaches a height of approximately 3 meters including normal pruning.

*Tree vigor*.—Moderately Vigorous. growth of approximately 1.5 to approximately 2 meters height the first growing season.

*Tree growth*.—Upright-spreading.

*Tree productivity*.—Productive. Fruit set is usually two or more times desired amount for marketable size fruit. Thinning and spacing of fruit is necessary.

*Tree form*.—Vase formed.

*Bearer*.—Regular. No alternate bearing observed.

*Fertility*.—Unknown. Should be planted with another variety to ensure consistent production.

*Tree canopy density*.—Medium-dense. Pruning is required to open tree vase shape, allowing more sunlight to center of tree.

*Tree hardiness*.—Hardy in all fruit growing areas of California. Winter chilling requirement is approximately 650 hours at or below 7.2° C.

*Tree disease resistance/susceptibility*.—No specific testing for relative plant disease resistance/susceptibility has been designed. Under close observation in Wasco, Kern County, Calif., no particular plant/fruit disease resistance/susceptibility has been observed.

Trunk: (measurements at 30 cm above soil line).

*Trunk diameter*.—Approximately 16 cm. Varies with soil type, fertility, climatic conditions and cultural practices.

*Trunk texture*.—Medium shaggy, increases with age of tree.

*Trunk color*.—Near Greyed-green 197D to near Greyed-green 197A on exposed areas and near Greyed-orange 164B in recesses. Becomes darker with age.

Branches: (measurements at approximately 90 cm above soil line).

*Branch size*.—Diameter ranged from approximately 7 to approximately 9 cm.

*Branch texture*.—Smooth on 1st year wood, increasing roughness with tree age.

*Branch color*.—Branches vary from near Greyed-green 197D to near Greyed-green 197A on exposed areas and near Greyed-orange 164B in recesses.

*Branch lenticels*.—Number: Numerous—varies from approximately 2 to approximately 9 per square centimeter. Lenticel number varies widely depending on environmental conditions and vigor of the plant. Color: Near Greyed-green 197A. Typical size: Approximately 6 mm in length and approximately 1.5 mm wide.

Flowering shoots: (data taken in July at midpoint of current-season growth).

*Flowering shoot size*.—Average diameter: approximately 5 mm.

*Flowering shoot color*.—Topside: Near Yellow-green 147B with highlights of near Greyed-red 180C. Underside: Near Yellow-green 147B.

*Flowering shoot lenticels*.—Plentiful; very small. Number varies from approximately 5 to approximately 18 per linear centimeter. Lenticel number varies widely depending on environmental conditions and vigor of the plant.

*Flowering shoot leaf buds*.—Shape: Pointed-obovate. Width: 1 mm. Length: Approximately 1.5 mm. Color: Near Greyed-orange 177A.

*Flowering shoot flower buds*.—Shape: Rounded-conical. Width: Approximately 0.5 mm. Length: Approximately 0.5 mm. Color: Near Greyed-orange 177A. Number per node: Usually 2.

LEAVES (data taken in July on fully expanded leaf at midpoint of current-season growth)

*Leaf size*.—Average length: Approximately 95 mm. Average width: Approximately 40 mm.

*Leaf thickness*.—Medium.

*Leaf color*.—Upper surface: Near Yellow-green 147A. Lower surface: Near Yellow-green 147B.

*Leaf form*.—Elliptic.

*Tip*.—Acuminate.

*Base*.—Cuspidate.

*Leaf margin/venation*.—Margin: Slightly serrated. Venation: Pinately net veined.

*Leaf surface texture*.—Smooth.

*Leaf petiole*.—Average length: Approximately 11 mm. Average diameter: Approximately 1.5 mm. Color: Near Greyed-red 180B, with green background.

*Leaf stipules*.—Absent.

*Leaf glands*.—Form: Globose. Number: Varies from approximately 4 to approximately 6. Position: Opposite on upper portion of petiole and base of leaf blade. Average size: Small, approximately 0.3 mm by approximately 0.3 mm. Color: Near Greyed-orange 166B.

FLOWERS (fully opened)

General:

*Flower blooming period*.—First bloom: Feb. 27, 2002. Full bloom: Mar. 2, 2002.

*Flower size*.—Average diameter: approximately 26 mm.

*Flower aroma*.—Very slight.

Flower peduncle:
*Length*.—Approximately 9 mm.
*Diameter*.—Approximately 1 mm.
*Color*.—Near Green 142A.
Flower petals:
*Number*.—Approximately 5.
*Arrangement*.—Slightly overlapping.
*Length*.—Approximately 11 mm.
*Diameter*.—Approximately 9 mm.
*Shape*.—Circular.
*Apex shape*.—Rounded.
*Base shape*.—Narrows at point of attachment.
*Color*.—White.
*Surface texture*.—Smooth.
*Margins*.—Smooth.
Flower sepals:
*Number*.—5.
*Length*.—Approximately 4.5 mm.
*Diameter*.—Approximately 2.5 mm.
*Shape*.—Obovate.
*Color*.—Near Green 142B.
*Surface texture*.—Smooth.
Flower stamens:
*Number*.—Approximately 24 to 29, average approximately 26.
*Average length*.—Approximately 7 mm.
*Filament color*.—White.
*Anther color*.—Near Greyed-yellow 160B.
*Pollen color*.—Near Greyed-yellow 160B.
Flower pistil:
*Number*.—Usually one, occasionally two.
*Average length*.—Approximately 9 mm.
*Ovary diameter*.—Approximately 1 mm.
*Pubescence*.—None.
*Stigma position*.—Extends below anthers.

FRUIT (data taken at firm-ripe on mature tree managed to obtain maximum quality)

General:
*Fruit harvest*.—Date of first pick: Approximately Jun. 16, 2002. Date of last pick: Approximately Jun. 22, 2002.
Fruit size:
*Length* (*stem end to apex*).—Approximately 62 mm.
*Diameter in line with suture plane*.—Approximately 66 mm.
*Diameter perpendicular to suture plane*.—Approximately 66 mm.
*Average weight*.—Approximately 160 gm.
Fruit form:
*Viewed from apex*.—Rounded, symmetrical.
*Viewed from side, facing suture*.—Rounded, almost symmetrical.
*Viewed from side, perpendicular to suture*.—Rounded, symmetrical.
Fruit apex shape: Rounded, to slightly flattened.
Fruit stem-end cavity depth: Shallow.
Fruit stem:
*Length*.—Approximately 8 mm.
*Diameter*.—Approximately 2 mm.
*Color*.—Near Green 143C.
Fruit skin:
*Thickness*.—Medium.
*Adherence to flesh*.—Tenacious.
*Surface texture*.—Smooth.
*Pubescence*.—None.
*Bloom*.—Moderate amount.
*Ground color*.—Rarely visible, but near Yellow-orange 23C when visible.
*Overcolor*.—Near Greyed-purple 187B, becoming black when fully ripe.
*Taste*.—Mildly bitter.
Fruit flesh:
*Ripens*.—Evenly.
*Texture*.—Fine, firm, crisp and juicy.
*Fibers*.—Few.
*Flavor*.—Mildly sweet.
*Brix*.—Approximately 18 degrees.
*Juice*.—Plentiful.
*Aroma*.—Slight.
*Color*.—Amber (near Greyed-yellow 162C).
Fruit use: Dessert. Market, local and long distance.
Fruit shipping/keeping quality: Good. Holds well in cold storage for six weeks and maintains good firmness and eating quality. Minimal bruising and scarring in packing and shipping trials.
Stone: (measurements taken on dried stones).
*Stone freeness*.—Semi-freestone.
*Stone size*.—Length: Approximately 20 mm. Diameter in line with suture plane: Approximately 18 mm. Diameter perpendicular to suture plane: 5 mm. Stone Form (viewed from side): Rounded, asymmetrical.
*Stone form* (*viewed from stem end*).—Oval, nearly symmetrical.
*Stone base shape*.—Narrows to stem attachment, then flattened 4 mm at stem attachment.
*Stone apex shape*.—Rounded with a small dull point.
*Stone surface*.—Irregularly furrowed near base. Lightly ridged toward base. Lightly pitted throughout.
*Stone halves*.—Nearly equal.
*Stone ridges*.—One on each side of the suture, small and narrow, beginning at the base and extending throughout the length of the stone.
*Stone outgrowing keel*.—Well developed.
*Stone tendency to split*.—Slight.
*Stone color*.—Near Greyed-orange 165C when dried.

What is claimed is:

1. A new and distinct variety of plum tree named 'Suplumthirtyfive' as herein illustrated and described.

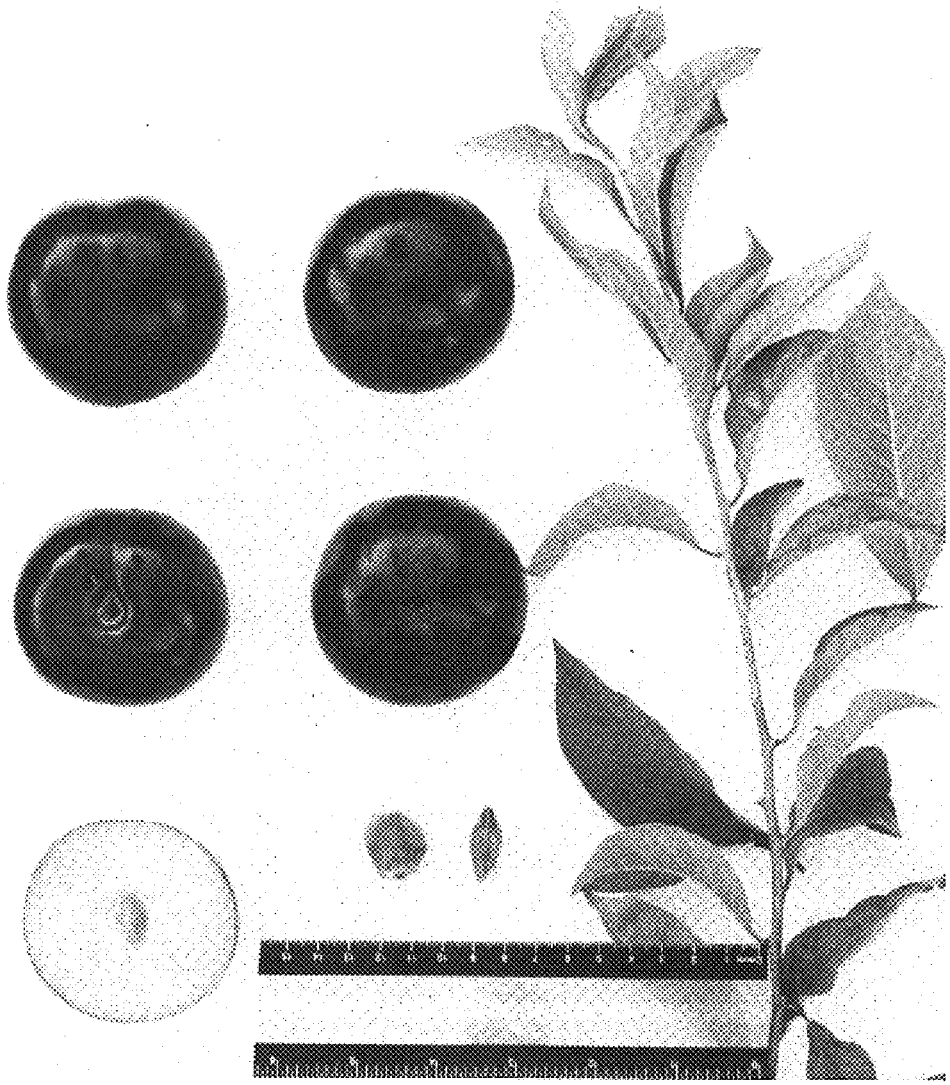

* * * * *